(12) United States Patent
Ladebeck

(10) Patent No.: US 6,529,762 B1
(45) Date of Patent: Mar. 4, 2003

(54) METHOD FOR THE OPERATION OF AN MR TOMOGRAPHY APPARATUS

(75) Inventor: Ralf Ladebeck, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/658,797

(22) Filed: Sep. 11, 2000

(30) Foreign Application Priority Data

Sep. 10, 1999 (DE) .......................................... 199 43 404

(51) Int. Cl.[7] .............................................. A61B 5/055
(52) U.S. Cl. ...................... 600/410; 600/414; 324/309
(58) Field of Search ................. 600/410, 414; 324/307, 309, 318, 322

(56) References Cited

U.S. PATENT DOCUMENTS

| 5,049,147 | A | * | 9/1991 | Danon ........................... 606/10 |
| 5,601,619 | A | * | 2/1997 | Drechsler ...................... 607/88 |
| 5,818,231 | A | | 10/1998 | Smith |
| 5,947,900 | A | * | 9/1999 | Derbyshire et al. .......... 324/309 |
| 6,275,035 | B1 | * | 8/2001 | Debbins et al. ............... 324/307 |

OTHER PUBLICATIONS

"Automatic Computerized Radiographic Identification of Cephalometric Landmarks," Rudolph et al., American Journal of Orthodontic Dentofacial Orthopedy, vol. 113(2), pp. 173–179, Feb. 1998.

"Investigation of Filter Sets for Supervised Pixel Classification of Cephalometric Landmarks by Spatial Spectroscopy," Rudolph et al., International Journal of Medical Informatics, vol. 7, No. 3, pp. 183–191 (1997).

* cited by examiner

Primary Examiner—Ruth S. Smith
(74) Attorney, Agent, or Firm—Schiff Hardin & Waite

(57) ABSTRACT

In a method for the operation of a MR tomography apparatus the MR tomography apparatus determines anatomical landmarks in the examination subject on the basis of a specific diagnostic interrogatory prescribed by the user. Measuring parameters for following MR measurements are defined automatically on the basis of these landmarks.

6 Claims, 1 Drawing Sheet

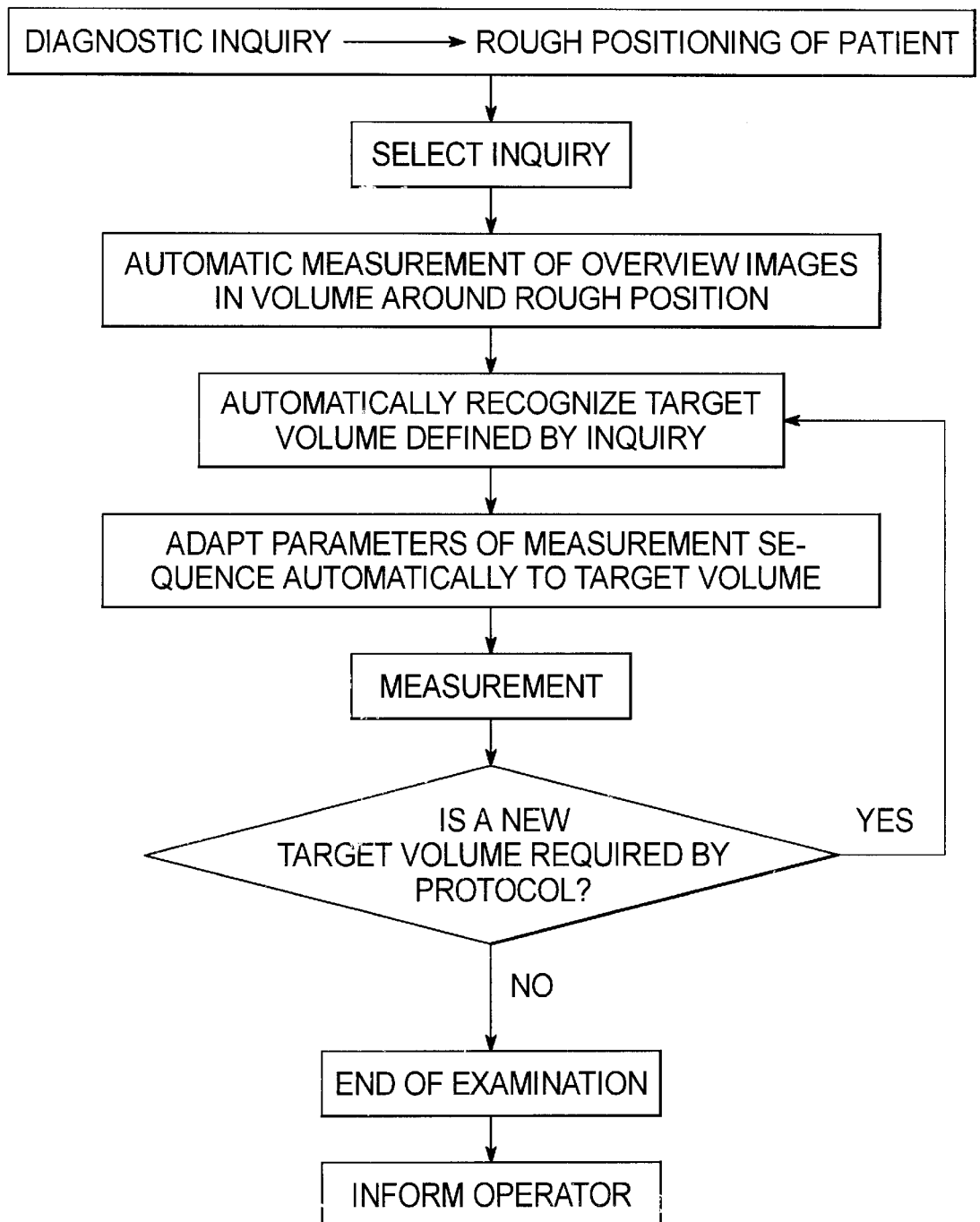

METHOD FOR THE OPERATION OF AN MR TOMOGRAPHY APPARATUS

BACKGROUND OF THE INVENTION

1. Field of the Invention

The present invention is directed to a method for operating a magnetic resonance (MR) tomography apparatus.

2. Description of the Related Art

Heretofore the implementation of a magnetic resonance (MR) examination has ensued interactively. Overview (planning) images are registered at the beginning of the examination. The slices/volumes to be examined are then defined based on these overview images. Saturation slices are also defined in many examinations in order, for example, to avoid artifacts due to fat tissue. These saturation slices are also defined by the user of the apparatus on the basis of the anatomical details seen in the overview images. It often occurs that the slices to be measured and other image parameters cannot yet be adequately defined on the basis of the overview images. One person therefore usually must be available during the entire examination time only for operating the apparatus. Typically, this person cannot attend to any other jobs for the time of the examination.

High demands are made as to the qualifications of the operator since the diagnostic content of the exposures that are obtained is greatly dependent on the positioning of the slices to be measured and on the saturation slices (if required) as well as on other parameters to be set (slice thickness, number of slices, distance between the slices, observation window, size of the measuring matrix, etc.).

This job is in fact somewhat facilitated by making prepared measuring protocols available, which already contain pre-settings. Typically, image parameters such as matrix size, type of pulse sequence, repetition time, etc., are thereby prescribed. Nonetheless, the adaptation of these prepared measuring protocols to a specific examination case requires the input of a number of parameters, which requires the interaction of a specifically trained and experienced operator during the entire measuring time.

U.S. Pat. No. 5,818,231 discloses a method for the quantification and standardization of magnetic resonance measurements. The method can be employed for medical as well as for industrial magnetic resonance applications and can define the value of a continuous property such as concentration, viscosity or the like. This occurs by interpolation or extrapolation from a model that was in turn derived from training datasets. Pattern recognition methods are thereby employed. A number of low-resolution scan are interpreted instead of identifying material composition with a single, high-resolution scan. The combination of such scans, which are implemented with different modalities, generally leads to more exact results than a single high-resolution scan.

SUMMARY OF THE INVENTION

It is an object of the present invention to provide a method that simplifies the operation of an MR tomography apparatus and makes interaction of the operator largely unnecessary during the execution of the measurement or scan.

The above object is achieved in accordance with the principles of present invention in a method for operating magnetic resonance tomography apparatus, wherein the tomography apparatus determines anatomical landmarks in the examination subject automatically on the basis of a specific diagnostic interrogatory which is predetermined and entered by an operator, and the tomography apparatus also automatically determines measuring parameters for the following magnetic resonance measurements on the basis of these landmarks.

In the inventive method, the user need only indicate the diagnostic question (inquiry or interrogatory) for standard examinations; the entire measuring procedure then sequences automatically. For standard examinations, the operator therefore can turn to other tasks during the measuring time, for example operating a second MR apparatus. Fewer demands are made on the operator, at least for standard measurements.

The method can be especially advantageously utilized when the inquiry refers to a specific organ whose position and expanse in the examination subject is determined by the MR apparatus on the basis of a comparison of an overview exposure to stored patterns. The measuring parameters that are optimum for the organ to be imaged thus can be independently determined by the MR tomography apparatus.

DESCRIPTION OF THE DRAWING

The single FIGURE is a flow chart of an exemplary embodiment of the inventive method.

DETAILED DESCRIPTION OF THE PREFERRED EMBODIMENTS

The figure shows the executive sequence of an automated measurement as an example. In the first method step, a rough positioning of the patient is carried in conformity with the diagnostic inquiry, so that, for example, the head or the knee of the patient is positioned such that it comes to lie in the observation window. Subsequently, for example organ-specifically, the respective diagnostic inquiry is selected. In most instances, diagnostic inquiries can be based on standardized measuring executions. For example, approximately 90% of the examinations ensue according to the same executive sequence in the case of head examinations.

An automatic measurement of overview images then ensues in the volume around the predetermined rough position. Anatomical landmarks are then identified on the basis of these overview images. These landmarks can, for example, be the outside contour of the brain, of the articular cleft of the knee, etc. Techniques for identifying such landmarks are described, for example, by Rudolph, D. J. et al in the article "Automatic Computerized Radiographic Identification of Cephalometric Landmarks" in American Journal of Orthodental Dentofacial Orthopedy, 113 (2), 173–9, February 1998 and are likewise described by Rudolph, D. J. et al in the article "Investigation of Filter sets for supervised pixel classification of cephalometric landmarks by spatial spectroscopy" in International Journal of Medical Informatics (1997), Volume 47, No. 3, Pages 183 through 191. The target volume defined with the diagnostic interrogatory is thus automatically recognized.

The parameters of the following measuring sequence are then adapted—likewise automatically—to the recognized target volume. A number of parameters are taken into consideration for this purpose. Dependent on the automatically identified position and alignment of the subject under examination, the position, the expanse and the inclination of the observation window to be measured is defined such that the entire, previously defined region, i.e., for example, the organ to be imaged, is covered in the following measuring execution. For determining the suitable parameters for a current patient, the currently acquired overview images can be correlated with stored overview images. A transformation of the current images thereby ensues by displacement, rotation and stretching. When the transformation having the best correlation coefficient has been found, the corresponding transformation coefficients are applied to the observation window and to the slice position.

Saturation slices are also produced in many MR measurements, with the transverse magnetization in these slices being saturated so that no signal contribution occurs from these slices. For example, the signal from fat layers, that is otherwise disturbing because it is very bright, can be blanked out. These saturation slices likewise can be automatically positioned. Dependent on the application, the optimum position is defined such that pre-defined landmarks are covered and/or other landmarks (for example, the organ to be imaged) are not affected and/or such that the saturation slices lie in a specific direction relative to other landmarks.

The measuring sequence may require that alternative procedures automatically be activated when the identified, optimum parameters cannot be realized. If, for example, the necessary number of slices cannot be measured within the repetition time TR that has been set, a determination can be made to lengthen the repetition time TR or to increase the slice spacing or the slice thickness.

After the MR tomography apparatus has automatically determined the parameters for the MR measurement on the basis of the pre-selected diagnostic interrogatory, the measurement itself can be likewise automatically started.

The diagnostic interrogatory can require measurements in a number of target volumes. In this case, the measuring procedure in turn branches back for the recognition of a new target volume. Otherwise, the end of the examination implementation has been reached and the operator is informed thereof. The operator is likewise informed if malfunctions occurred during the measuring execution. As a result, the operator no longer need be present during the measurement but can perform other tasks. In contrast to conventional MR systems, a constant presence of an operator during the measurement is not required for a majority of the MR measurements; rather, the operator can turn to other jobs. A significantly lower qualification of the operator is required for a number of standard examinations, and the examinations become more reproducible.

Although other modifications and changes may be suggested by those skilled in the art, it is the intention of the inventor to embody within the patent warranted hereon all changes and modifications as reasonably and properly come within the scope of their contribution to the art.

I claim:

1. A method for operating a magnetic resonance tomography apparatus comprising the steps of:

storing respective standardized patterns for different anatomical structures in said magnetic resonance tomography apparatus;

entering a diagnostic interrogatory requesting Imaging of a specified one of said different anatomical structures into a control unit of said magnetic resonance tomography apparatus;

conducting an overview exposure of a subject, said overview exposure including naturally occurring anatomical landmarks having respective physical locations in said subject;

automatically identifying said physical locations of said anatomical landmarks in said subject from said overview exposure;

automatically identifying said specified one of said anatomical structures in said overview exposure by automatically comparing said overview exposure to the standardized pattern for said specified one of said anatomical structures, and automatically identifying a location of a target volume, containing said specified one of said anatomical structures, in said subject from said naturally occurring landmarks in said overview exposure; and automatically determining measuring parameters for a tomographic magnetic resonance measurement of said specified one of said anatomical structures from the identification of said target volume.

2. A method as claimed in claim 1, comprising identifying said specified one of said anatomical structures in said subject by correlating data obtained in said overview exposure to said standardized pattern for said specified one of said anatomical structures by transformation with displacement, rotation and stretching.

3. A method as claimed in claim 2, comprising obtaining transformation coefficients from said correlation, and employing said transformation coefficients to set geometrical imaging parameters for said magnetic resonance measurement.

4. A method as claimed in claim 1, wherein the step of automatically determining measuring parameters for said magnetic resonance measurement comprises automatically determining at least one parameter selected from the group consisting of slice position, slice orientation, number of slices, slice thickness, saturation slices and repetition time.

5. A method as claimed in claim 1, comprising automatically emitting a signal if a malfunction occurs in said magnetic resonance measurement.

6. A method as claimed in claim 1, comprising generating a signal when said magnetic resonance measurement is completed.

* * * * *